(12) United States Patent
Delaire et al.

(10) Patent No.: US 9,366,629 B2
(45) Date of Patent: Jun. 14, 2016

(54) LEAD ASSAY

(75) Inventors: Jacques Delaire, Palaiseau (FR); Isabelle Leray, Issy les Moulineaux (FR); Jean-Pierre Lefevre, Puteaux (FR); Liyun Zhao, Oxford (GB); Ting Wu, Cachan (FR)

(73) Assignee: CENTRE NATIONAL DE LA RECHERCHE SCIENTIFIQUE—CNRS, Paris (FR)

( * ) Notice: Subject to any disclaimer, the term of this patent is extended or adjusted under 35 U.S.C. 154(b) by 83 days.

(21) Appl. No.: 13/139,364

(22) PCT Filed: Dec. 8, 2009

(86) PCT No.: PCT/FR2009/052450
§ 371 (c)(1),
(2), (4) Date: Aug. 2, 2011

(87) PCT Pub. No.: WO2010/067012
PCT Pub. Date: Jun. 17, 2010

(65) Prior Publication Data
US 2011/0294222 A1 Dec. 1, 2011

(30) Foreign Application Priority Data
Dec. 11, 2008 (FR) ...................................... 08 06954

(51) Int. Cl.
*G01N 21/64* (2006.01)
*B01F 5/06* (2006.01)
(Continued)

(52) U.S. Cl.
CPC .............. *G01N 21/643* (2013.01); *B01F 5/061* (2013.01); *B01F 13/0059* (2013.01);
(Continued)

(58) Field of Classification Search
CPC ....... G01N 31/22; G01N 33/20; G01N 33/84; G01N 21/78; G01N 21/29; G01N 33/1813; G01N 33/2864; G01N 1/4077
USPC ..................................................... 436/73, 77
See application file for complete search history.

(56) References Cited

U.S. PATENT DOCUMENTS 4,154,675 A * 5/1979 Jowett et al. ................... 210/675
5,019,516 A * 5/1991 Wiese .............................. 436/77
(Continued)

FOREIGN PATENT DOCUMENTS

JP     57-196151     12/1982
JP     H09-061416     3/1997
(Continued)

OTHER PUBLICATIONS

Lead and Mercury Sensing by Calixarene-Based Fluoroionophores Bearing Two or Four Dansyl Fluorophores Remi Metivier, Isabelle Leray, and Bernard Valeur Chem. Eur. J. 2004, 10, 4480-4490.*

(Continued)

*Primary Examiner* — Lyle Alexander
*Assistant Examiner* — Dwan A Gerido
(74) *Attorney, Agent, or Firm* — Young & Thompson (57) ABSTRACT

Process for metering lead in a sample of original water, in which is placed a sample of the water of which at least a substantial portion of the colloidal and organic material is passed in solution (sample of pretreated water), having: a first stage, starting from a sample of pretreated water with an adjusted pH, the lead is concentrated and the other parasitic ions are at least partially eliminated to obtain a sample of water that is concentrated with lead and substantially lacking in other parasitic ions (sample of lead-concentrated water); and a second stage in which, starting from the sample of lead-concentrated water, the sample of lead-concentrated water is mixed with a selective, lead-sensitive fluorescent probe whose fluorescence intensity/lead metering function is known; then, the thus produced water/fluorescent probe mixture is excited by the light, and the fluorescence intensity of the thus excited water/fluorescent probe mixture is collected optically; finally, starting from the thus detected fluorescence intensity, the lead metering of the sample to be metered is determined based on the fluorescence intensity/lead metering function.

16 Claims, 4 Drawing Sheets

(51) Int. Cl.
*B01F 13/00* (2006.01)
*G01N 31/22* (2006.01)
*G01N 33/18* (2006.01)
*G01N 1/40* (2006.01)
*G01N 21/77* (2006.01)

(52) U.S. Cl.
CPC .............. *G01N 21/645* (2013.01); *G01N 31/22* (2013.01); *G01N 33/1813* (2013.01); *B01F 2005/0621* (2013.01); *B01F 2005/0636* (2013.01); *B01L 2200/027* (2013.01); *B01L 2200/10* (2013.01); *B01L 2300/0654* (2013.01); *B01L 2300/0816* (2013.01); *B01L 2300/0867* (2013.01); *B01L 2400/086* (2013.01); *G01N 1/405* (2013.01); *G01N 1/4044* (2013.01); *G01N 2021/7786* (2013.01)

(56) References Cited

U.S. PATENT DOCUMENTS

| | | | | |
|---|---|---|---|---|
| 5,205,987 | A | * | 4/1993 | Ashraf-Khorassani et al. .......................... 422/83 |
| 5,354,652 | A | * | 10/1994 | Silbergeld ........................ 435/4 |
| 2008/0280366 | A1 | | 11/2008 | Demas et al. |

FOREIGN PATENT DOCUMENTS

| | | |
|---|---|---|
| JP | 2000-221180 | 8/2000 |
| JP | 2005-031050 | 2/2005 |
| JP | 2005-265523 | 9/2005 |

OTHER PUBLICATIONS

Chemical modification of silica surface by immobilization of functional groups for extractive concentration of metal ions P.K. Jal, S. Patel, B.K. Mishra Talanta 62 (2004) 1005-1028.*

International Search Report, dated Apr. 21, 2010, from corresponding PCT application.

In-Hyoung Chang et al., "Miniaturized Lead Sensor Based on Lead-Specific DNAzyme in a Nanocapillary Interconnected Microfluidic Device", Environ. Sci. Technol., Apr. 15, 2005, pp. 3756-3761, vol. 39, No. 10, XP-002542230; Cited in International Search Report.

"Detection de cations polluants a l'aide de fluoroionophores selectifs", Epreuve Commune de Tipe 2005—Partie D, 2005, pp. 10-15, XP-002542450; Cited in International Search Report.

Martin Telting-Diaz et al., "Mass-Produced Ionophore-Based Fluorescent Microspheres for Trace Level Determination of Lead Ions", Analytical Chemistry, Oct. 15, 2002, pp. 5251-5256, vol. 74, No. 20, XP-002542452; Cited in International Search Report.

Yi Lu et al., "New highly sensitive and selective catalytic DNA biosensors for metal ions", Biosensors and Bioelectronics, May 1, 2003, pp. 529-540, vol. 18, No. 5/06, XP-001182221; Cited in International Search Report.

Emilie Destandau et al., "A novel microfluidic flow-injection analysis device with fluorescence detection for cation sensing. Application to potassium", Analytical and Bioanalytical Chmistry, Feb. 8, 2007, pp. 2627-2632, XP-019488814; Cited in International Search Report.

Abraham D. Stroock, et al.; "Chaotic Mixer for Microchannels"; www.sciencemag.org; vol. 295; Jan. 25, 2002; pp. 647-651.

* cited by examiner

LEAD ASSAY

The invention relates to the metering of lead.

Its object is more particularly a process for metering lead in water or in a solid sample and a device for metering lead for the implementation of the process.

The water whose lead is to be metered is typically river water, surface water, tap water, drinking water, etc. The solid sample whose lead is to be metered is typically paint, soil, etc.

Processes and devices for metering by spectroscopy of adsorption or atomic emission are already known. This technique allows good selectivity, and in the case of lead, excellent sensitivity (for example, 1 µg of lead per liter, or 1 ppb). The operating devices are typically intended for the laboratory and are both expensive and bulky, such that they are not transportable. Furthermore, the metering operations are long. These processes and devices are therefore not suitable in the case of a metering of lead in situ by means of a portable device, of low cost, fast to operate but with sufficient sensitivity relative to the standards of the material.

Processes and portable devices for metering lead electrochemically are also known. According to the embodiments, the devices in question have a sensitivity that ranges from 0.1 µg to 2 µg; they require the use of a mercury electrode, with the inherent problems, or they require a period of analysis that exceeds 3 to 5 minutes, which makes them unsuited for use in situ in which it should be possible to perform the analysis quickly, or else they are expensive and complicated to use.

"Lead and Mercury Sensing by Calixarene-Based Fluoroionophores Bearing Two or Four Dansyl Fluorophores," published in *Chemistry—A European Journal*, 2004, 10, pages 4480 to 4490, presents photophysical and complex properties of fluorescent probes derived from calixarenes and in particular the selectivity and the sensitivity of the compound Calix-DANS4 for lead. A complete device for metering lead that is suitable for a metering in situ is therefore not described. As for the synthesis of these calixarenes, it was described in *Chem. Commun.* 2003, 996 (Métivier, Leray and Valeur). The object of the document XP-002542450 "Détection de cations polluants á l'aide de fluoroionophores sélectifs [Detection of Polluting Cations Using Selective Fluoroionophores]" (common test of TIPE 2005—Part D) is the use of the compound Calix-DANS4, and it is covered by the above-cited publications.

"A Novel Microfluidic Flow-Injection Analysis Device with Fluorescence Detection for Cation Sensing," published in *Analytical & Bioanalytical Chemistry*, 2007, 387:2627, pages 2627 to 2632, presents a microfluidic device for the detection of potassium ions by fluorimetry. Such a device comprises two inputs, a mixing zone, and a chamber for measuring fluorescence intensity, with which optical excitation means and means for collecting and analyzing fluorescence intensity after excitation are associated. Such a device is equipped in this case for the metering of potassium ions but not for lead.

"Miniaturized Lead Sensor Based on Lead-Specific DNAzyme in a Nanocapillary Interconnected Microfluidic Device," published in *Environmental Science & Technology*, 2005, 10, pages 3756 to 3761, presents a process for metering lead in which, in a first stage, the lead is concentrated, and, in a second stage, water from the lead-concentrated water sample is mixed with a selective lead-sensitive fluorescent probe; the thus produced water/fluorescent probe mixture is excited by light, and the fluorescence intensity of the thus excited water/fluorescent probe mixture is collected optically, and the lead metering of the sample to be metered is determined, based on the fluorescence intensity/lead metering function. In the described embodiment, the excitation source is an ionized argon laser that prevents this process from being implemented by means of a portable device. In addition, the process requires using a microscope and two high-voltage feeds, one for capillary electrophoresis (in the event of pre-separation and preconcentration) and one for introducing the sample through the nanoporous membrane. Finally, the process requires using a specific DNAzyme of the lead with its substrate.

It is also possible to cite the following documents in the prior art:

"Chaotic Mixer for Microchannels," published in *Science*, Vol. 295, 2002, pages 647 to 651;

"Rate of Access to the Binding Sites in Organically Modified Silicates," published in *Chem. Mater.* 2002, 14, pages 2757 to 2766;

"Mass-Produced Ionophore-Based Fluorescent Microspheres for Trace Level Determination of Lead Ions," published in *Anal. Chem.* Vol. 74, No. 20, Oct. 15, 2002, pages 5251 to 5256, that rests on a measurement of fluorescence in a circulation tank that is therefore not microfluidic;

"New Highly Sensitive and Selective Catalytic DNA Biosensors for Metal Ions," published in *Biosensors & Bioelectronics*, Elsevier B V N L, Vol. 18, No. 5/06, May 1, 2003, pages 529 to 540;

"A Novel Microfluidic Flow-Injection Analysis Device with Fluorescence Detection for Cation Sensing. Application to Potassium," published by *Anal Bional Chem.*, Spinger, Feb. 8, 2007, pages 2627 to 2632, which relates to a microfluidic sensor for the detection of potassium;

US2008/0280366, which describes a method for detection of lead by "clusters" fluorescence $(Pb_4Br_{11})^{3-}$.

There is therefore a need to meter the lead in situ by means of a device that is portable, of low cost, fast to operate, and with sufficient sensitivity relative to the standards on the subject. Actually, lead is a very toxic heavy metal and the cause of different very negative effects on human health (behavior problems, epilepsy, saturnism . . . ). Lead can be found in water (river water, surface water, tap water, drinking water . . . ) or in a solid substrate such as paint, soil . . . . According to European standards, the boundary content of lead allowed in water for human consumption that in the past was 50 µg of lead per liter (or 50 ppb) was limited starting from the end of 2003 to 25 µg of lead per liter (or 25 ppb) and will be lowered further to 10 µg of lead per liter (or 10 ppb) starting at the end of 2013. Consequently, the metering of lead is to be able to be done under numerous circumstances, on the field, under occasionally difficult conditions, quickly and simply, and finely reliably and precisely. The devices that are implemented are to be compact and easily transportable. They should also be able to be manufactured in large numbers and not generate toxic waste.

The object of the invention is to meet this need.

For this purpose, according to a first aspect, the object of the invention is a process for metering lead in a sample of water such as river water, surface water, tap water, drinking water, etc. (sample of original water), in which a sample of the water of which it is desired to meter the lead is placed and of which at least a substantial portion of the colloidal and organic material is passed in solution (sample of pretreated water), with the process comprising the following successive stages:

A first stage in which, starting from a sample of pretreated water with an adjusted pH, the lead is concentrated to obtain a sample of lead-concentrated water; and A second stage in which, starting from the sample of lead-concentrated water:

First, water from the lead-concentrated water sample is mixed with a selective, lead-sensitive fluorescent probe whose fluorescence intensity/lead metering function is known, Then, the thus produced water/fluorescent probe mixture is excited by the light, and the fluorescence intensity of the thus excited water/fluorescent probe mixture is collected optically, Finally, starting from the thus detected fluorescence intensity, the lead metering of the sample to be metered is determined based on the fluorescence intensity/lead metering function, characterized in that in the first stage:

In a first sub-stage, the lead is adsorbed by passing the sample of pretreated water with an adjusted pH over a selective adsorbent that does not fix the other parasitic ions;

Then, in a second sub-stage, a desorption of the lead (sample of lead-concentrated water) is initiated;

The other parasitic ions are at least partially eliminated to obtain a sample of water that is concentrated in lead and that is substantially lacking in other parasitic ions.

The lead is adsorbed by passing the sample of pretreated water with adjusted pH over functionalized silica balls; and desorption by elution is initiated, with the eluant being acidified water, to obtain a lead-concentrated water sample.

According to the embodiments, in the first stage, the lead is concentrated with a concentration factor of at least 25; the calcium and sodium ions are eliminated at least partially, and the parasitic ions that may interfere with lead in the second stage of analysis by fluorescence are eliminated to a concentration where these parasitic ions are such that the implementation of the second stage of analysis by fluorescence is possible.

In addition, according to one embodiment, the first stage comprises a third sub-stage in which filtration of the elution water obtained by the desorption of the second sub-stage is initiated, followed by a fourth sub-stage in which the filtrate of the third sub-stage is supplemented with a solution of 3-chloropyridine in acetonitrile, with the final pH being 3.

According to one embodiment, a start is made from a sample of original water, and, in a preliminary stage, at least a substantial portion of the colloidal and organic material is put into solution by an acidification sub-stage followed by a mineralization sub-stage (pretreated water sample). In this case, and according to one embodiment, the preliminary stage consists in an acidification by the addition of ultra-pure concentrated nitric acid (69% $HNO_3$), at ambient temperature, for a period on the order of one hour, and at a pH that is less than 2. According to another embodiment, the preliminary stage consists of an acidification sub-stage with a pH that is less than 2, by addition of nitric acid and a mineralization sub-stage by addition on the order of 2% oxidized water, at a temperature on the order of 80° C., and for a period on the order of one hour.

According to one embodiment, after the preliminary stage and before the first stage, the pH of the sample of pretreated water is brought to a value on the order of 10, in particular by adding soda.

According to another characteristic, the pH is adjusted to approximately 3 for the second stage.

According to one embodiment, the fluorescent probe is the fluoroionophore Calix-DANS4, in solution in a solvent that is a mixture of acetonitrile and water at a pH of 3 in the mixture, and at a concentration of approximately $2\times10^{-6}$ M. In this case, in the sample of lead-concentrated water, the calcium concentration is less than 100 mg/liter, and the sodium concentration is less than 11.5 mg/l, taking into account the selectivity of the fluorescent probe.

According to one embodiment, the second stage is carried out in a microfluidic device.

According to one embodiment, the water/fluorescent probe mixture is excited by light by means of a light diode, and the fluorescence intensity of the thus excited water/fluorescent probe mixture is collected by means of an optical fiber with which a photodetector is associated.

With the process according to the invention as described, it is possible to detect the lead up to a metering of 2 micrograms per liter of water, of which it is desired to meter the lead.

According to a second aspect, the object of the invention is a device for metering lead in water such as surface water, drinking water, etc., for the implementation of the process that was just described, which comprises:

A first upstream functional unit that can allow the implementation of the first stage of the process, and A second downstream functional unit that can allow the implementation of the second stage of the process, whereby this second unit comprises:

A microfluidic device that has, on the one hand, an input for the sample of lead-concentrated water and, on the other hand, an input for the fluorescent probe, and, from upstream to downstream and in fluid communication, a zone for mixing water and the fluorescent probe, a chamber for measuring the fluorescence intensity, and an output of residues, Light means for excitation of the water/fluorescent probe mixture and means for collecting the fluorescence intensity of the thus excited water/fluorescent probe mixture that are associated either transversally to the measuring chamber or perpendicularly to one another, the excitation being achieved in the plane of the measuring chamber and the collection of the emission being achieved in a direction that is perpendicular to this chamber, And calculating means that are programmed for, based on the detected fluorescence intensity, determining the lead metering of the sample to be metered, based on the function of fluorescence intensity/lead metering of the fluorescent probe, in which the first unit comprises at least one capillary that forms a functionalized silica microball micro-column through which the sample of the pretreated water can pass.

According to one embodiment, the mixing zone of the microfluidic device comprises active or passive mixing means, in particular integrated mixing chevrons.

According to one embodiment, the chamber for measuring the fluorescence intensity of the microfluidic device is enlarged and comprises integrated flux distributors.

According to one embodiment, the light means for excitation of the water/fluorescent probe mixture comprise at least one light diode that is associated with at least one optical fiber for excitation and in that the means for collecting the fluorescence intensity of the water/fluorescent probe mixture comprise at least one photodetector that is associated with at least one optical fiber for collection.

According to a suitable embodiment in the case of the process that includes a preliminary stage, as was described above, the device also comprises, upstream from the first unit, a preliminary unit that can allow the implementation of this preliminary stage.

According to one embodiment, the device forms an at least partially integrated, compact and manually portable unit.

According to a third aspect, the object of the invention is a process for metering lead in a solid substrate, in which:

The lead is extracted in advance from the solid substrate, and it is solubilized in water that does not contain lead;

Then, the process for metering lead in water is implemented as it was described above.

Now, several embodiments of the invention are described using drawings in which.

The process for metering the lead that is found in a water sample that is conventionally referred to as a sample of original water is now described. As indicated, the water, as appropriate, is river water, surface water, tap water, drinking water, or any other water in which it is desired to meter the lead, in particular for health purposes.

This sample of original water is taken in situ, and the process is implemented in situ by means of a metering device 1. If necessary, the sample of original water is transported into a location where the metering is carried out. Taking into account the process that is implemented, it is possible that the metering device 1 is manually portable, forming a unit that is at least partially integrated and compact, for example housed in a casing 2. This metering device 1 can therefore be transported into any desired location and in particular in situ instead of taking the original sample to be metered.

Starting from the sample of original water and in a preliminary pretreatment stage, at least a substantial portion of the colloidal and organic material that it contains is put into solution. For this purpose, it is possible, according to one embodiment, to initiate an acidification by addition of ultra-pure concentrated nitric acid (69% $HNO_3$), at ambient temperature, for a period on the order of one hour, and at a pH of less than 2.

According to a variant with heating and addition of oxidized water, first a sub-stage of acidification at a pH of less than 2 is implemented by addition of ultra-pure, concentrated nitric acid (69% $HNO_3$), and then a sub-stage of mineralization is implemented by addition of a quantity of 2% oxidized water, at a temperature of 80° C., and for a period of 1 hour.

Thus, at least a substantial portion of the colloidal and organic material of the sample of original water is passed in solution. After this preliminary stage of pretreatment, the thus obtained water sample is conventionally referred to as a sample of pretreated water.

It may be that the colloidal and organic material has already been solubilized in the sample of original water or that it has not been or that it has been, which is not a problem for the implementation of the process. In this case, the preliminary pretreatment stage that was just described is not implemented. Nevertheless, for the rest of the description, it is conventionally considered that the preliminary pretreatment stage was done and that a sample of pretreated water is consequently available.

After this preliminary stage and/or before a first stage of the process, the pH of the sample of pretreated water is brought to the value of 10, in particular by adding a base such as soda, potash, or ammonia.

A water sample that is conventionally referred to as a sample of pretreated water with an adjusted pH is thus obtained.

The pH value of 10 was determined to allow total adsorption of lead in the first subsequent stage of the process.

In the casing 2, the metering device 1 comprises a preliminary functional unit of input 3, able to allow the implementation of the preliminary pretreatment stage followed by the adjustment of the pH. This preliminary functional unit of input 3 (left part of FIG. 1) is functionally placed upstream from a functional unit that is conventionally referred to as the first functional preconcentration unit 4.

Actually, the process then comprises a first stage in which, starting from the sample of pretreated water with a pH that is adjusted to a value that is close to 10, the lead is concentrated at the same time that the other parasitic ions are at least partially eliminated. By this first stage, a water sample conventionally referred to as a lead-concentrated water sample is obtained.

To do this, and in a first sub-stage, the lead ions $Pb^{2+}$ of the sample are adsorbed by passing the sample of pretreated water, with a pH that is adjusted to a value that is close to 10, over a selective adsorbent that does not fix the other parasitic ions.

Then, in a second sub-stage, a desorption of the lead by elution using a tiny volume of an acid solution is initiated. Typically, for 25 ml of a sample of pretreated water that has circulated in the column, the volume of the eluate is 0.5 ml, which leads to a concentration factor of 50. At pH 2, all of the previously adsorbed lead is desorbed below.

Then, in a third sub-stage, a filtration of the elution water is initiated.

Finally, in a fourth sub-stage, the filtrate is supplemented with a solution of 3-chloropyridine in acetonitrile so that at the end, the final pH of the new solution is 3 in a mixture of acetonitrile (60% by volume) and water (40% by volume). The use of this buffer avoids adding alkaline or alkaline-earth ions that can interfere with the lead below.

At the end of this fourth sub-stage, following the addition of a small volume of water, the concentration factor was reduced from 50 to 31.25, i.e., it is at least 25.

Figure 1:
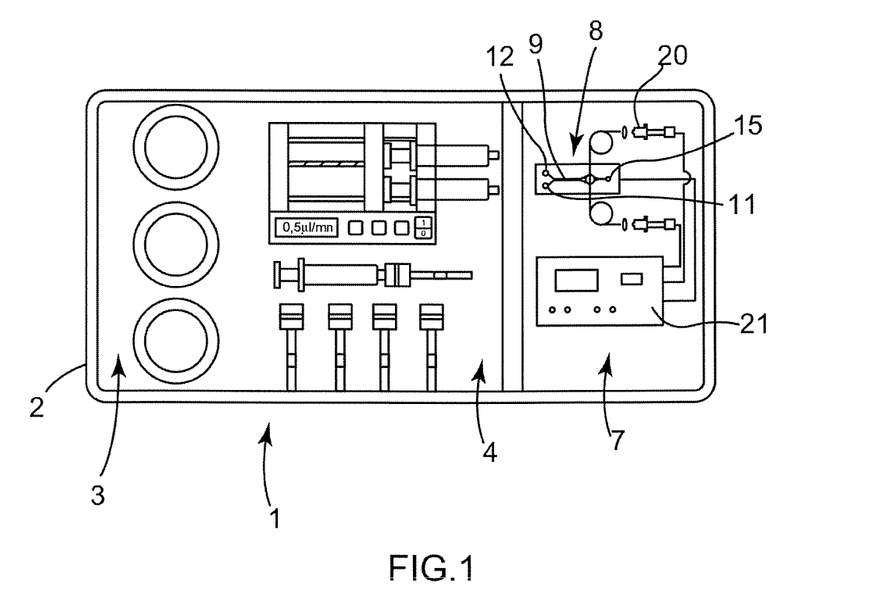
FIG. 1 is a diagrammatic elevation view of a lead metering device according to the invention, comprising the first upstream functional unit and the second downstream functional unit, as well as a preliminary unit that is upstream from the first unit, whereby this device is suitable in the case where the process comprises the above-mentioned preliminary stage.

These sub-stages are implemented in the first operational preconcentration unit 4 (central portion of FIG. 1).

For this purpose, and relative to the first and second sub-stages, the sample of pretreated water with a pH that is adjusted to a value that is close to 10 is passed over the silica microballs that are functionalized with 3-aminopropyl groups, ref. Aldrich 36,425-8. Alternatively, it is possible to consider the use of nanoporous silica balls that are functionalized with specific ligands of the heavy metals that are to be detected. Consequently, the expression "silica microballs" is to be interpreted in a functional way and includes any equivalent structure.

Then, desorption by elution is initiated, the eluant being pure water that is acidified to a pH that is close to 2, for example an aqueous solution of perchloric acid. Thus, after filtration and adjustment of the pH to 3 by addition of 3-chloropyridine in a mixture of acetonitrile/water that is 60/40 by volume, what has been referred to as the sample of lead-concentrated water is obtained.

Figure 2:
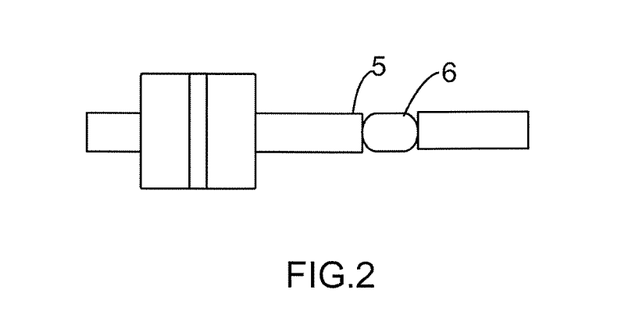
FIG. 2 is a diagrammatic elevation view of a portion of the first functional unit.

In one embodiment and as shown diagrammatically in FIG. 2, the first preconcentration unit 4 comprises at least one capillary 5, for example made of polytetrafluoroethylene (PTFE), constricted by clamping at one end, forming or including a microcolumn 6 of functionalized silica microballs. The sample of water that is pretreated at a pH that is adjusted to a value of close to 10 can pass through this capillary 5. The lead, and optionally other heavy metals, is adsorbed on the surface of the functionalized silica microballs. By contrast, the calcium and sodium ions, often present in water in large excess, are not trapped by the functionalized silica microballs so that these ions are eliminated from the eluate once desorption is done.

To prevent the functionalized silica microball micro-column 6 from becoming clogged by the colloidal and organic material present in the sample of original water, the pretreatment, whose function is to solubilize this material, was implemented as mentioned above.

The filtration that takes place after the desorption is implemented by means of, for example, a cellulose nitrate filter that has a pore size of 0.45 µm.

The filtrate is supplemented by a solution of 3-chloropyridine in acetonitrile to ensure that at the end, the pH of the new solution is 3 in a mixture of acetonitrile (60% by volume) and water (40% by volume). This mixture of solvents will be the same as the mixture that is used for dissolving the fluorescent probe in the second stage of analysis so as to prevent thermal effects in the microfluidic channel.

The lead concentration produced under such conditions is achieved with a concentration factor of at least 25 and more especially equal to or on the order of 30.

In contrast, simultaneously and by adsorption/desorption operation, the calcium and sodium ions are eliminated at least partially and, more generally, the parasitic ions that can interfere with the lead in the second stage of the process that consists of analysis by fluorescence are eliminated. This elimination is done up to a concentration where these parasitic ions are such that the implementation of this second stage is possible; i.e., it makes it possible to decelerate a significant fluorescence intensity of the effective lead content. Actually, it was noted that the calcium ion interferes with the lead at certain concentrations but not at others, so that is appropriate to limit the concentration of the calcium ion to a value below which it does not interfere with lead.

Of course, the operating conditions of the adsorption, desorption and filtration described above are optimized, in particular regarding the stream in the microball column 6 or the perchloric acid concentration in the eluant solution.

The process then comprises the previously mentioned second stage in which, starting from the sample of lead-concentrated water (or analyte) that has a pH that is adjusted to 3 by preliminary addition of the 3-chloropyridine buffer, an analysis of lead by fluorescence is initiated.

This second stage is implemented in a second functional analysis unit 7. This second unit 7 (right portion of FIG. 1) is placed functionally downstream from the first preconcentration unit 4.

Figure 3:
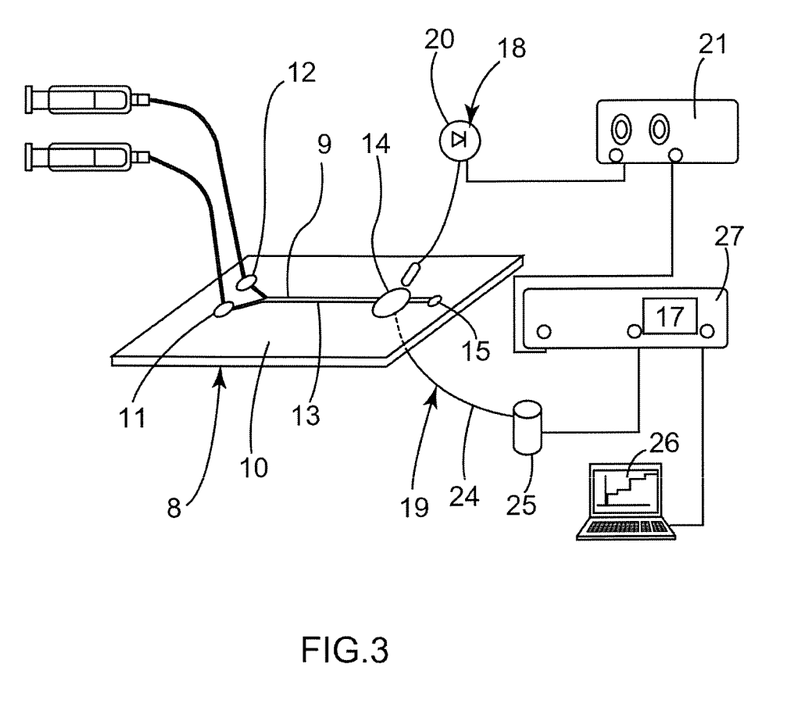
FIG. 3 is a diagrammatic perspective view of the second functional unit.

The second analysis stage is implemented by means of a selective, lead-sensitive fluorescent probe and a microfluidic device 8 that is part of the second analysis unit 7.

Figure 6:
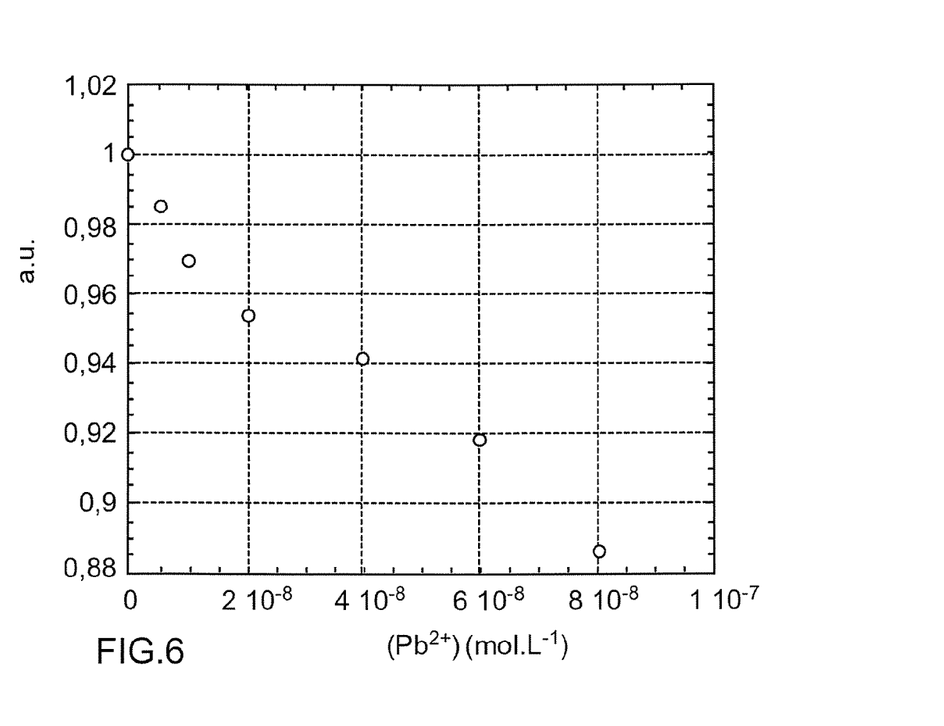
FIG. 6 is a calibration curve of the microfluidic device of the second functional unit.

The fluorescence intensity/lead metering function of the selective lead-sensitive fluorescent probe is known or has been otherwise established. This function can be illustrated by a calibration curve such as the one that is shown in FIG. 6. It is noted in this case that this curve is close to a decreasing linear function. Thus, it is possible, knowing this function or this curve, based on a given fluorescence intensity, because it is so noted, to determine without a risk of error and with precision the lead metering that corresponds to this fluorescence intensity. This function or this curve can be loaded in the programmed calculating means.

The second analysis stage itself comprises three successive sub-stages: a first sub-stage for mixing the sample of lead-concentrated water with the selective, lead-sensitive fluorescent probe; a second sub-stage for excitation by the light of this mixture and optical collection of the fluorescence intensity of the thus excited mixture; and finally, a third sub-stage for determining the lead metering of the sample to be metered, starting from the fluorescence intensity/lead metering function that was previously the function in question.

The fluorescent probe is the fluoroionophore Calix-DANS4 in solution in a solvent that is a mixture of acetonitrile (60% by volume) and water (40% by volume) at a pH of 3 in the mixture and at a concentration of $2 \times 10^{-6}$ M.

The structural formula of the Calix-DANS4/lead complex is as follows:

In this case in question, it is possible, taking into account the selectivity of the fluorescent probe relative to the lead, that in the sample of lead-concentrated water, the calcium concentration is or can be less than 100 mg/liter, and the concentration of sodium is or can be less than 11.5 mg/l.

As has been indicated, an acidic pH of 3 was retained. Actually, the pH of use of the fluorescent probe is an important parameter because the complexing of lead by the four nitrogens fixed on the dansyl groups is particularly sensitive to pH. An acidic pH tends not to allow the complexing of lead, while nitrogens are protonated. A basic pH does not have this effect but tends to cause the variation of fluorescence noted after optical excitation not to be sufficient. Since, as in this case, light excitation is produced at a wavelength of 365 nm and detection is done at a wavelength of greater than 515 nm, it was noted that a pH of 3 was preferable for ensuring an effective metering by fluorescence.

Figure 4:
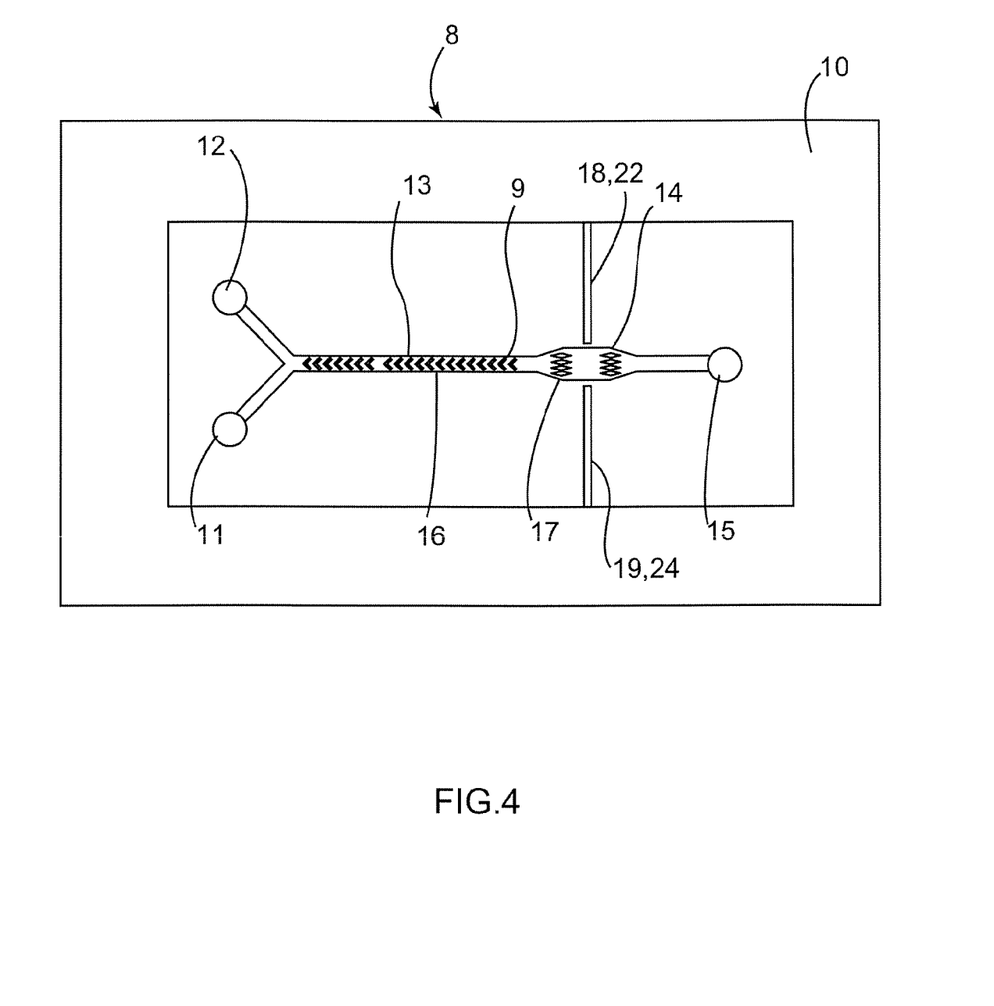
FIG. 4 is a diagrammatic elevation view of the microfluidic device of the second functional unit.

The microfluidic device 8 comes in the form of a Y-shaped micro-pipe 9 that is molded in a material such as a silicone polymer such as polydimethylsiloxane (known under the acronym PDMS) fixed on a glass substrate 10. As a variant, the microfluidic device 8 comes in the form of a micro-pipe 9 that begins in a Y shape and continues in a path with a suitable length that is selected for implementing a total complexing reaction.

The micro-pipe 9 comprises an input 11 for the sample of lead-concentrated water (analyte) and an input 12 for the fluorescent probe (reactive).

From upstream to downstream and in fluid communication, the micro-pipe 9 comprises an elongated zone 13 for mixing water and the fluorescent probe, an enlarged chamber 14 for measuring the fluorescence intensity, and an output 15 of residues.

In the embodiment shown in FIG. 4, it is provided that the mixing zone 13 is equipped with internal mixing chevrons 16, able to ensure the reactive/analyte mixture in a passive manner. Of course, another active or passive mixing structure can be provided instead.

Figure 5:
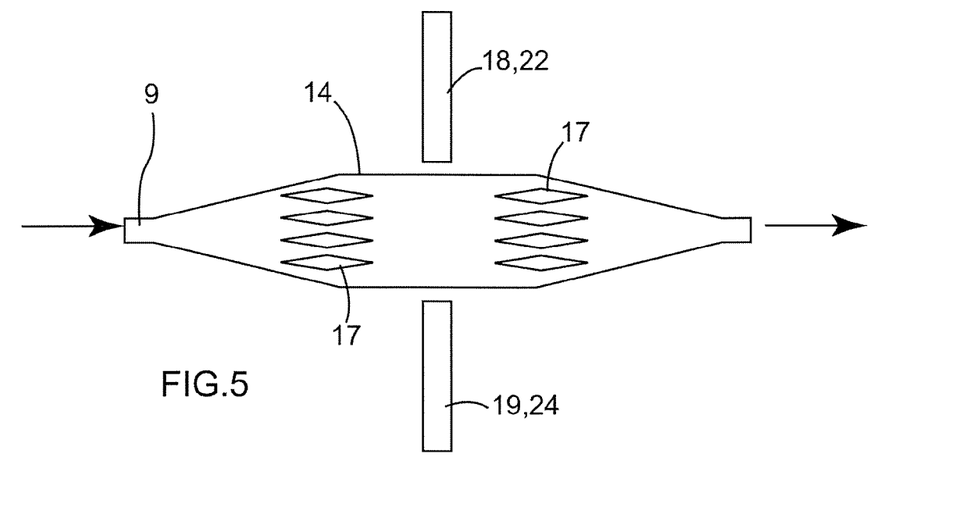
FIG. 5 is a diagrammatic elevation view of the measuring chamber of the microfluidic device of the second functional unit.

In the embodiment shown in FIG. 5, it is provided that the measuring chamber 14 is enlarged and comprises one or more flux distributors 17 in the form of deflectors.

Associated with the microfluidic device 8 are, on the one hand, light means 18 for excitation of the water/fluorescent probe mixture, and, on the other hand, optical means 19 for collecting the fluorescence intensity of the water/fluorescent probe mixture.

These light excitation means 18 and optical means 19 for collecting the fluorescence intensity are associated either transversally to the measuring chamber 14, in particular downstream from a flux distributor 17, or perpendicularly to one another, whereby the excitation is done in the plane of the measuring chamber and the collection of the emission is done in a direction that is perpendicular to this chamber.

According to one embodiment, the light excitation means 18 comprise at least one light diode 20, with which power supply 21 and an optical excitation fiber 22, and, if necessary, a lens 23, are associated.

In this embodiment, the light diode 20 is selected for emitting at 365 nm.

According to one embodiment, the optical means 19 for collecting the fluorescence intensity comprise an optical fiber for conductive collecting 24, arranged orthogonally relative to the optical excitation fiber 22, with which a photodetector 25 is associated, in front of which a high-pass optical fiber 28 ($\lambda$>515 nm) is arranged.

Calculating means 26 that are programmed for, based on the detected and collected fluorescence intensity, determining the lead metering of the sample to be metered, starting from the fluorescence intensity/lead metering function of the fluorescent probe, loaded in means 26, are also associated with the microfluidic device 8. These calculating means 26, such as a computer, comprise means for display, storage, and printing of data.

In addition, an amplifier with synchronous detection 27 makes it possible to be free of background noise.

It is understood that the stages of the previously described process can be integrated in a more or less significant way, which then involves integrating, in a more or less elevated way, the microfluidic device 8 in the metering device 1. Thus, the microfluidic device 8 could be designed with a single input for the sample to be metered, while a fluorescent probe reserve would be integrated into the metering device 1, with the microfluidic device 8 being equipped with suitable valves, gates . . . .

With the process according to the invention as described, it is possible to detect lead up to a metering of 2 µg per liter of water in which it is desired to meter the lead, which is well above the threshold required for the drinking water by standards for 2013, or 10 µg per liter of water.

Furthermore, the process has the advantage of being selective of the lead. Actually, the metering of the lead can be carried out despite the presence in the water of calcium and sodium, up to concentrations of 11.5 mg per liter of water for the former and 100 mg per liter of water for the latter.

Even assuming that other heavy metal ions that are present in the trace state, such as lead, were preconcentrated after passing into the microcolumn, they would not be detected during the second stage, taking into account the selectivity of the fluorescent probe for the lead.

According to a development of the invention, the process for metering the lead is intended for a solid substrate, such as paint, soil, etc.

In this case, the lead is extracted in advance from a sample of the solid substrate, and it is solubilized in water that does not contain lead. Then, the process for metering lead in water as it was described above is implemented.

The invention claimed is:

1. Process for metering lead Pb2+ in a sample of water containing lead Pb2+, said process comprising the following successive stages:

providing the sample of water containing lead Pb2+;

performing stage (A) of obtaining a lead-concentrated water sample with a lead concentration factor of at least 25, by concentrating the lead Pb2+ of said sample of water; and performing stage (B) with the following sequential steps:

mixing water from the lead-concentrated water sample with a selective, lead-sensitive fluorescent probe with a known fluorescence intensity/lead metering function to produce a water/fluorescent probe mixture, exciting the thus-produced water/fluorescent probe mixture by light, and optically collecting a resulting fluorescence intensity of the thus-excited water/fluorescent probe mixture to determine a detected fluorescence intensity, and starting from the thus-detected fluorescence intensity, the lead metering of the sample to be metered is determined based on the fluorescence intensity/lead metering function, wherein stage (A) is performed as follows:

a first sub-stage (A1) of passing said sample of water containing lead Pb2+ as received in the providing step, over a selective adsorbent that does not fix other parasitic ions to thereby adsorb the lead Pb2+ from said sample of water on the selective adsorbent, wherein said selective adsorbent is functionalized silica balls, and a second sub-stage (A2) of initiating a desorption of the lead Pb2+ with an eluent to thereby obtain the lead-concentrated water sample that is concentrated with the lead Pb2+ and that is substantially lacking in other parasitic ions.

2. The process according to claim 1, wherein, in sub-stages (A1) and (A2), the functionalized silica balls are functionalized with 3-aminopropyl groups; and the eluant is acidified water.

3. The process according to claim 1, wherein in stage (A), calcium and sodium ions in the lead-concentrated water sample are at least partially eliminated.

4. The process according to claim 1, wherein in stage (A), parasitic ions that may interfere with lead Pb2+ in stage (B) of analysis by fluorescence are eliminated to a concentration where said parasitic ions are such that implementation of stage (B) of analysis by fluorescence is possible.

5. The process according to claim 1, wherein stage (A) comprises a third sub-stage (A3) of initiating filtration of the lead-concentrated water sample obtained by the desorption of the second sub-stage (A2) to thereby obtain a filtrate.

6. The process according to claim 5, wherein the third sub-stage (A3) is followed by a fourth sub-stage (A4) in which the filtrate is supplemented by a 3-chloropyridine solution in acetonitrile to obtain a final pH of 3.

7. The process according to claim 1, wherein, in a preliminary stage, at least a substantial portion of colloidal and organic material contained in the first sample of water is put into solution to thereby obtain pretreated water.

8. The process according to claim 7, wherein said substantial portion of colloidal and organic material is put into solution by acidification by addition of ultra-pure concentrated nitric acid (69% $HNO_3$), at ambient temperature, for a period on the order of one hour, and at a pH of less than 2.

9. The process according to claim 7, wherein said substantial portion of colloidal and organic material is put into solution by acidification at a pH of less than 2 by addition of nitric acid and mineralized by addition on the order of 2% oxidized water, at a temperature on the order of 80° C., for a period on the order of one hour.

10. The process according to claim 1, wherein before stage (A), the pH of the first sample of water is brought to a value on the order of 10.

11. The process according to claim 1, wherein for stage (B), the pH of the lead-concentrated water sample is adjusted to approximately 3.

12. The process according to claim 1, wherein the fluorescent probe is the fluoroionophore Calix-DANS4, in solution in a solvent that is a mixture of acetonitrile and water at a pH of 3 in the mixture.

13. The process according to claim 1, wherein the fluorescent probe has a concentration of approximately $2\times10^{-6}$ M.

14. The process according to claim 1, wherein in the lead-concentrated water sample, the concentration of calcium is less than 100 mg/liter, and the concentration of sodium is less than 11.5 mg/l.

15. The process according to claim 1, wherein the lead Pb2+ is detected up to a metering of 2 µg per liter of water.

16. Process for metering lead in a solid substrate, wherein:
the lead is extracted in advance from the solid substrate, and the lead is solubilized in water that does not contain lead;
after the lead is extracted and solubilized, the process for metering lead in water is implemented according to claim 1.

* * * * *